United States Patent
Krauss et al.

Patent Number: 5,222,484
Date of Patent: Jun. 29, 1993

[54] APPARATUS FOR SHOCK WAVE TREATMENT

[75] Inventors: Werner Krauss, Knittlingen; Helmut Wurster, Oberderdingen; Thomas Belikan, Knittlingen; Joachim Fladl, Oberderdingen, all of Fed. Rep. of Germany

[73] Assignee: Richard Wolf GmbH, Knittlingen, Fed. Rep. of Germany

[21] Appl. No.: 666,384

[22] Filed: Mar. 8, 1991

[30] Foreign Application Priority Data

Mar. 10, 1990 [DE] Fed. Rep. of Germany ....... 4007669

[51] Int. Cl.$^5$ .............................................. A61B 17/22
[52] U.S. Cl. ........................... 128/24 EL; 128/660.03; 378/62
[58] Field of Search ......... 128/24 EL, 660.01, 660.03; 378/62, 63, 121, 125, 126

[56] References Cited

U.S. PATENT DOCUMENTS

| | | | |
|---|---|---|---|
| 4,986,275 | 1/1991 | Ishida et al. | 128/660.03 |
| 5,060,634 | 10/1991 | Belikan et al. | 128/660.03 |
| 5,060,650 | 10/1991 | Wurster et al. | 128/660.03 |

FOREIGN PATENT DOCUMENTS

| | | |
|---|---|---|
| 3503702 | 8/1986 | Fed. Rep. of Germany . |
| 3826709 | 2/1989 | Fed. Rep. of Germany . |
| 3934105A1 | 10/1989 | Fed. Rep. of Germany . |
| 3840077 | 5/1990 | Fed. Rep. of Germany . |

Primary Examiner—Lee S. Cohen
Assistant Examiner—Krista M. Pfaffle
Attorney, Agent, or Firm—Cohen, Pontani, Lieberman, Pavane

[57] ABSTRACT

An apparatus for shock wave treatment includes a shock wave transducer with a cup-shaped body and with an X-ray location finding device for finding the location of a bodily concretion or tissue to be treated. The X-ray device includes an extensible X-ray tube with telescoping tube sections which are sealed against an acoustic coupling medium filling the delay path of the transducer by a balloon arranged within the X-ray tube. The balloon is secured to the upper section of the tube and to the lower section thereof. Overpressure or underpressure is applied to the interior of the X-ray tube to adjust its length in order to optimise X-ray location finding on the one hand, and shock wave treatment on the other hand.

8 Claims, 2 Drawing Sheets

APPARATUS FOR SHOCK WAVE TREATMENT

BACKGROUND OF THE INVENTION

1. Field of the Invention

The invention concerns apparatus for shock wave treatment including an ultrasonic shock wave transducer having a delay path filled with an acoustic coupling medium enclosed by a membrane which is arranged to be placed on the body of a patient to be treated by means of shock waves generated by the transducer. The invention relates in particular to an X-ray device in such apparatus, for locating a concretion or tissue in the patient's body, to be destroyed by the shock waves, the device comprising an X-ray source having a tube which can be filled with an X-ray loss-free medium, for example a gas, and being arranged within the delay path and sealed against the coupling medium.

2. Description of the Related Art

Such apparatus have two location finding devices for finding the location of a concretion or tissue, namely an ultrasonic location finding device and an X-ray location finding device which extend through the cup-shaped body of the shock wave transducer, and into the delay path thereof. The tube is closed at its end facing the membrane. The tube and a balloon are sealed against the coupling medium of the delay path and can be filled with a gas, for example air, so as to cause as little absorption as possible of the X-rays. During operation, the tube and the balloon are filled with gas in such a way that the balloon expands and comes to rest against the inner side of the membrane and thus indirectly against the body of the patient to be treated, so that the liquid coupling medium within the delay path which is strongly X-ray absorbent is almost completely displaced from the path of the X-rays.

The location of the concretion or tissues by X-rays is considerably improved because the X-rays pass through the gas and are, therefore, subjected to substantially less absorption than would be the case if they were to pass through the coupling medium which is a liquid. The tube however, being of sufficient length to enable efficient X-ray location, causes fade out of a relatively large part of the sonic field of the shock wave transducer. Such fade out is also caused by the balloon. Thus to shorten the tube whilst correspondingly enlarging the balloon would not serve to avoid fade out of the sonic field, because for X-ray location finding, the balloon must be expanded to such an extent that it can no longer adapt to the X-ray cone and so fades out a substantial part of the sonic field. Such fading out of the sonic field can affect the efficiency of shock wave therapy.

SUMMARY OF THE INVENTION

The invention is intended to provide an X-ray location device in apparatus of the kind described above, which device ensures that both shock wave therapy and the X-ray location of a concretion or tissues can be carried out under optimum conditions, without interference therebetween.

According to the present invention, the X-ray tube is of variable length in its axial direction within the delay path. Thus the length of the X-ray tube can be reduced for shock therapy to an extent that the sonic field of the shock wave transducer is unreduced or is only slightly reduced. Although such shortening of the X-ray tube allows further use of the X-ray location finding device, the resolution of the X-ray image is reduced because coupling medium is disposed in the path of the X-rays. If better resolution is needed, the length of the X-ray tube must be increased in the direction of the membrane in order to displace the liquid coupling medium. By changing the length of the X-ray tube, both the X-ray location finding as well as the shock wave, can be optimised.

The length of the X-ray tube can be made variable by virtue of a telescopic construction thereof, wherein the tube has a plurality of longitudinally slidably interfitting sections. The tube length can thus be continuously changed. The X-ray source itself requires no constructional modification so that for example generically similar ultrasonic shock wave apparatus of older construction can readily be provided with the extensible X-ray tube.

The X-ray tube preferably consists of concentric tubular sections the diameters of which are chosen to correspond to the enlargement of the X-ray beam towards the membrane.

The length of the X-ray tube can be adjusted by applying overpressure or underpressure therein. Thereby the length of the tube can be continuously altered and mechanical drive means need not be provided in the area of the delay path. A change in the length of the X-ray tube in the direction towards the membrane which seals off the cup-shaped body of the transducer, enables ready discharge of the coupling medium displaced by the tube in the delay path, and the medium is returned into the delay path when the tube is retracted again. To this end an equalising reservoir divided into two chambers may be provided, one of the chambers being connected through pipes to the delay path and the other chamber being connected to the interior of the X-ray tube which is sealed by an elastic membrane, or the like.

Such an equalizing system is described in DE-A-39 34 105.4, which is incorporated herein by reference.

The X-ray tube may be fitted with an inflatable balloon which extends within the X-ray tube along the internal wall thereof and is secured in airtight fashion against the internal wall of the tube, for example by means of a clamping ring. The length of the tube can thus be changed by an overpressure or underpressure to the interior of the balloon. The balloon may serve to seal the tube with respect to the coupling medium within the delay path. The provision of sealing means between the individual sections of the tube is thereby avoided. The balloon may be of relatively thin construction, especially in the region of the wall of the tube, and for this purpose the balloon is supported by the tube wall over its entire circumference.

In order to be capable of changing the length of the tube, the balloon must be secured at the end of the tube nearest to the cup-shaped body, and fixed to the free end of the tube remote from the cup-shaped body, for example by means of a clamping ring.

DETAILED DESCRIPTION OF THE INVENTION

Figure 1:
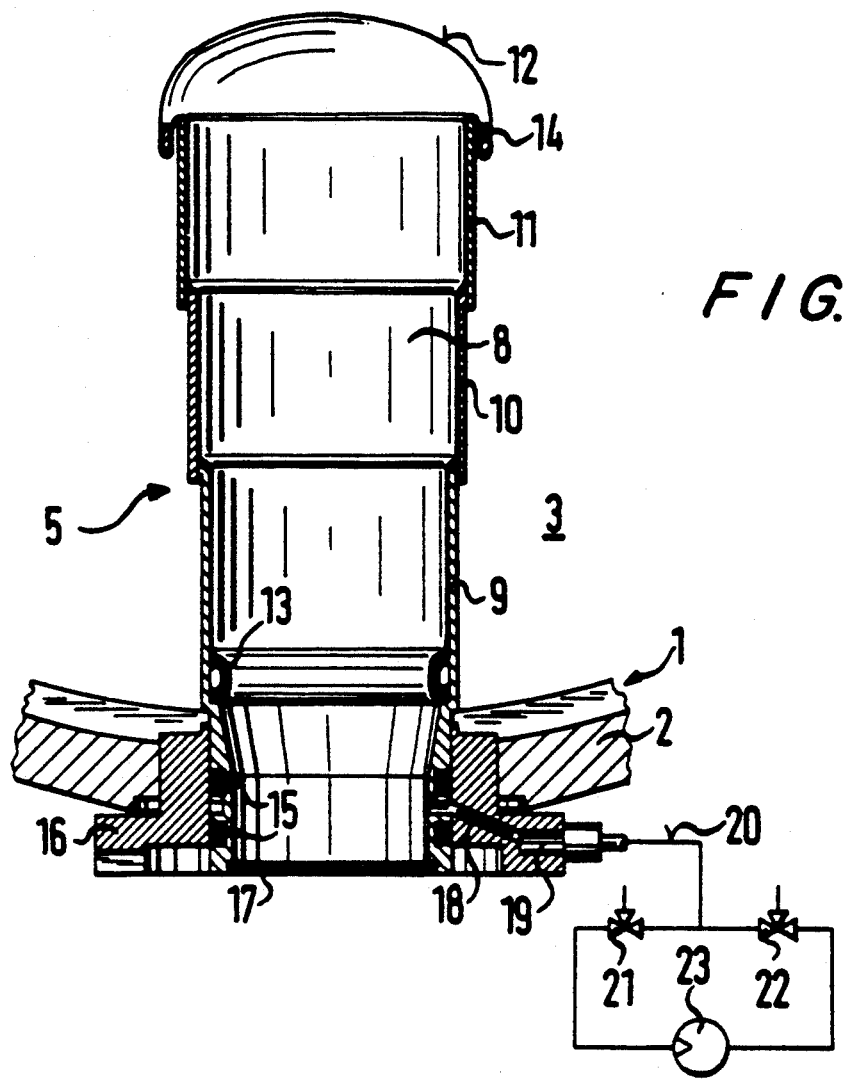
FIG. 1 is a sectional view of part of apparatus for ultrasonic shock wave treatment of a patient, with an X-ray location finding device part of which is integrated into a cup-shaped focusing body of a shock wave transducer, the X-ray device having a longitudinally expansible X-ray tube.
Figure 2:
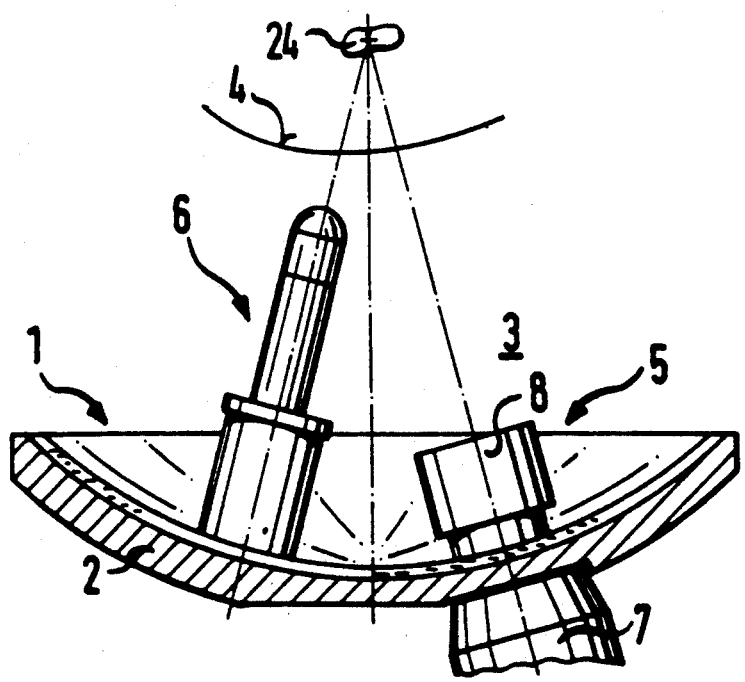
FIG. 2 is a schematic side view showing the cup-shaped body of a shock wave transducer in section, with the X-ray tube and an ultrasonic location finding device each in a retracted first end position.
Figure 3:
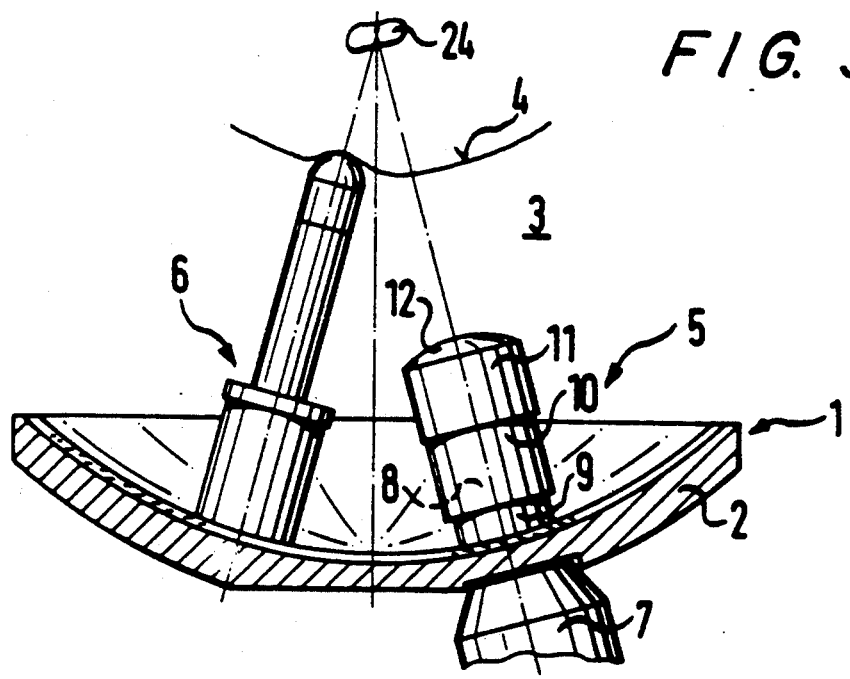
FIG. 3 is a similar view to that of FIG. 2 but showing the X-ray tube in a partially extended position and the ultrasonic location device in a fully extended end position.
Figure 4:
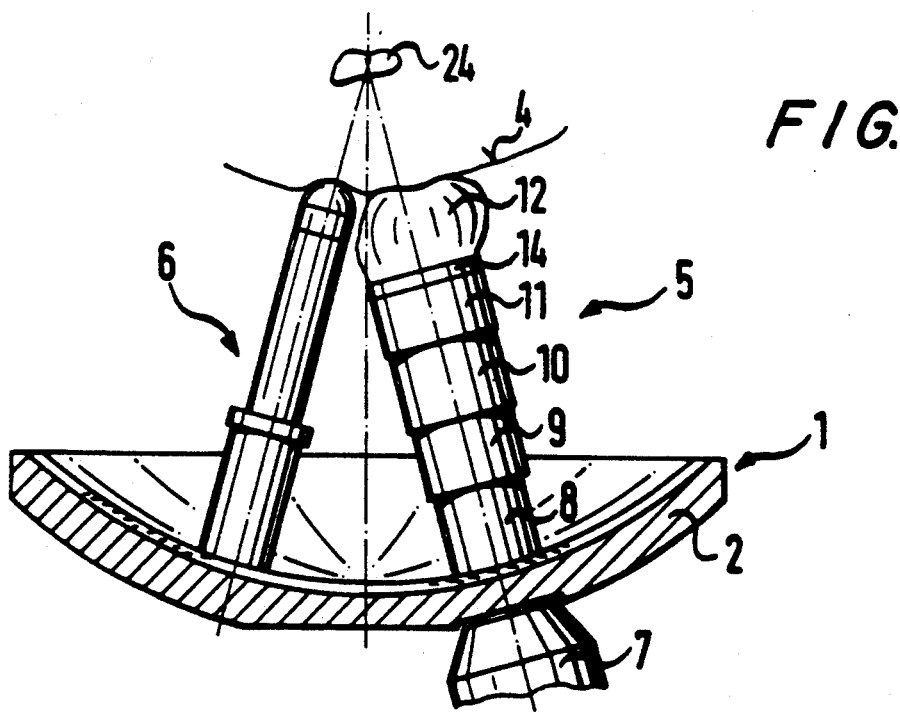
FIG. 4 is a similar view to that of FIG. 3 but showing the X-ray tube in a fully extended second end position.

As shown in FIG. 1, an ultrasonic shock wave transducer 1 comprises a cup-shaped focusing body 2 having an adjacent delay path filled with a liquid acoustic coupling medium 3 and being externally sealed by means of a membrane 4, as shown only schematically in FIGS. 2 to 4.

In order to carry out shock wave treatment on a patient, a concretion or tissue 24 to be treated must be located and brought to the focal point of the cup-shaped body 2. To this end, there are provided an X-ray location finding device 5 and an ultrasonic location finding device 6, which may extend through the cup-shaped body 2 or may be fixed thereto, so as to extend into the delay path.

Since the present invention relates specifically to the X-ray location finding device 5, the ultrasonic location finding device 6 will not be described in detail herein. Other location finding devices may be provided if need be and the ultrasonic location finding device 6 need not, of course, necessarily be provided.

The X-ray location finding device 5 has an X-ray source 7 essentially arranged outside the cup-shaped body 2, an adjustable length tube 8 of the X-ray source 7 extending into the delay path filled with the coupling medium 3. The X-ray tube 8, in the embodiment shown, consists of three telescoping, that is to say longitudinally slidably interfitting, tube sections 9, 10 and 11 concentrically arranged with respect to each other, to provide a telescope system as shown in FIG. 1. The number of the tube sections and their dimensions may be smaller or greater as required. Within the X-ray tube 8 provided by the tube sections 9, 10 and 11 is an elastic X-ray permeable balloon 12, made for example of latex, sealing the interior of the X-ray tube 8 against the coupling medium 3. The open lower end of the balloon 12 is firmly connected to the X-ray tube 8 by means of a first clamping ring 13 within the tube section 9 near the cup-shaped body 2, the clamping ring 13 pressing the part of the balloon 12 surrounding it in gas-tight fashion against the internal surface of the tube section 9.

The closed upper end of the balloon 12, which seals the tube 8 in gas-tight and fluid-tight fashion, extends over the outer surface of the upper end of the upper section 11, as a collar which is firmly urged against said outer surface by means of a second clamping ring 14 surrounding said outer surface.

The tube section 9 is seated in an annular base 16 and is sealed relative by means of rubber sealing rings 15. The base 16 is firmly and tightly seated in the cup-shaped body 2. The lower end of the X-ray tube 8, which is proximate to the body 2, is tightly sealed against the X-ray source 7 by means of an X-ray window 17.

Extending through the base 16 and the tube section 9 is a duct 18 connecting the interior of the tube 8 to a pump 23 by way of a connector 19, a pipe 20, and valves 21 and 22.

The valves 21 and 22 may be connected to the two chambers of an equalizing reservoir according to DE-A-39 34 105.4 which is incorporated herein by reference, one of the chambers being filled with gas and the other chamber with the liquid coupling medium 3.

By introducing gas into the X-ray tube 8, its length can be continuously adjusted between a retracted first end position as shown in FIG. 2 and a second fully extended end position as shown in FIG. 4 in which the closed end of the balloon 12, which seals the upper end of the X-ray tube 8, rests against the membrane 4. The further introduction of gas thereinto causes the balloon 12, which rests against the internal wall of the X-ray tube 8 and is radially supported by the tube sections 9, 10 and 11, to be completely unfolded or expanded so that the liquid coupling medium 3 is fully displaced whereby the upper end of the balloon 12 makes full surface to surface contact with the membrane 4 of the cup-shaped body 2. The X-ray tube 8 can be returned to its fully retracted position shown in FIG. 2 by evacuating the balloon 12 by way of duct 18 and the pipe 20.

FIGS. 2 to 4 show the ultrasonic location finding device 6 and the X-ray location finding device 5 in their different respective operating positions in which they are free of the membrane 4, in which positions there is no fading out of the sonic field, or only the slightest possible fading out thereof. This position of the devices 5 and 6 allows of in situ X-ray and ultrasonic location finding as well as particularly efficient shock wave application.

FIG. 3 shows the ultrasonic location finding device 6 in its position against the membrane 4. In this position of the device 6, the length of the X-ray tube 8 of the X-ray location finding device 5 is reduced by approximately half. This position of the devices 5 and 6 provides for optimum picture quality for the ultrasonic location finding device 6 and improved picture quality for the X-ray location finding device 5 as compared with the position of the devices 5 and 6 shown in FIG. 2, while the efficiency of application of the shock waves is only slightly reduced as a result of the fading out of the sonic field, caused by the location finding devices 5 and 6, and is still acceptable for effective shock wave treatment.

FIG. 4 shows both the ultrasonic location finding device 6 as well as the X-ray location finding device applied against the membrane 4.

This position of the devices 5 and 6 is optimum for taking a picture of the concretion or tissue 24 within the body of the patient to be treated, although efficient shockwave treatment cannot be carried out because the position of the devices 5 and 6 causes the sonic field to fade out.

By virtue of the continuous, longitudinal adjustability of the tube 8, the fading out of the sonic field can, for therapeutic purposes, be minimized, and for location finding purposes, the resolution of the X-ray device 5 can be optimized. Depending on the circumstances, the therapist can choose freely between the respective optima and thus optimize the treatment by locating the concretion or tissue 24 in one position of the devices 5 and 6 and destroying the concretion 24 by means of shock waves in another position of the devices 5 and 6.

What is claimed is:

1. An apparatus for ultrasonic shock wave treatment, comprising a shock wave transducer having a delay path comprising an acoustic coupling medium, and a membrane enclosing the delay path for placing against the body of a patient to be treated by shock waves generated by said transducer; an X-ray device for locating, in the patient's body, an object to be destroyed by said shock waves, the X-ray device comprising an X-ray source having an X-ray tube, an X-ray loss-free medium being contained in the X-ray tube, the X-ray tube being arranged within the delay path and comprising means for sealing the X-ray tube against the coupling medium, the X-ray tube having a length and an axial direction, further comprising means for variably adjusting the length of the X-ray tube in the delay path in the axial direction of the X-ray tube.

2. The invention as defined in claim 1, wherein the means for variably adjusting the length of the X-ray tube comprises a plurality of longitudinally slidably interfitting sections.

3. The invention as defined in claim 1, comprising means for applying variable pressure within the X-ray tube to adjust the length thereof in said axial direction.

4. The invention as defined in claim 1, wherein the sealing means is an inflatable balloon mounted on a free end of the X-ray tube, which end is directed towards the membrane.

5. The invention as defined in claim 4, wherein the balloon extends along an internal wall of the X-ray tube.

6. The invention as defined in claim 4, comprising a first clamping ring securing the balloon in gas-tight fashion against an internal wall of the X-ray tube at an end thereof remote from the membrane.

7. The invention as defined in claim 6, comprising a second clamping ring securing the balloon to the X-ray tube proximate to said free end thereof.

8. The invention as defined in claim 4, comprising a clamping ring securing the balloon to the X-ray tube proximate to said free end thereof.

* * * * *